United States Patent
Ferrari

(10) Patent No.: US 7,637,880 B2
(45) Date of Patent: Dec. 29, 2009

(54) DEVICE FOR THE EPICARDIAL SUPPORT AND/OR RESUMPTION OF CARDIAC ACTIVITY

(75) Inventor: Markus Ferrari, Jena (DE)

(73) Assignee: PPA Technologies AG, Jena (DE)

( * ) Notice: Subject to any disclaimer, the term of this patent is extended or adjusted under 35 U.S.C. 154(b) by 575 days.

(21) Appl. No.: 11/569,038

(22) PCT Filed: May 10, 2005

(86) PCT No.: PCT/EP2005/005053

§ 371 (c)(1), (2), (4) Date: Nov. 13, 2006

(87) PCT Pub. No.: WO2005/110514

PCT Pub. Date: Nov. 24, 2005

(65) Prior Publication Data

US 2008/0021259 A1      Jan. 24, 2008

(30) Foreign Application Priority Data

May 11, 2004      (DE) .................... 10 2004 023 191

(51) Int. Cl.
*A61M 1/10*      (2006.01)
(52) U.S. Cl. .................................... 601/153
(58) Field of Classification Search .................. 601/153
See application file for complete search history.

(56) References Cited

U.S. PATENT DOCUMENTS

| | | | |
|---|---|---|---|
| 3,513,836 A | | 5/1970 | Sausse |
| 5,713,954 A | * | 2/1998 | Rosenberg et al. ............ 600/17 |
| 5,738,627 A | | 4/1998 | Kovacs et al. |
| 7,060,023 B2 | * | 6/2006 | French et al. ................. 600/37 |
| 2007/0225545 A1 | * | 9/2007 | Ferrari ........................ 600/17 |

FOREIGN PATENT DOCUMENTS

| | | |
|---|---|---|
| DE | 19951220 A1 | 4/2001 |
| WO | 95 18593 A1 | 7/1995 |

* cited by examiner

*Primary Examiner*—Carl H Layno
*Assistant Examiner*—Yun Haeng Lee
(74) *Attorney, Agent, or Firm*—David S. Safran; Roberts Mlotkowski Safran & Cole, P.C.

(57) ABSTRACT

A device for epicardial support and/or the assuming of cardiac activity having a double membrane (1) having an elastic inner membrane (2) and a non-expandable outer membrane (3) as well as a closed cavity (4) formed therebetween which can be inflated and deflated by means of a fluid. With the objective of further developing a device of the type, so that same can more simply and at substantially lesser risk administer medication to the pericardial sac, a second cavity (7) having a fluid-permeable wall limiting the second cavity (7) relative to the heart is provided at the inward facing side (6) of the inner membrane (2) relative to the heart (5) with this second cavity (7) being able to be filled with a fluid through a separate fluid line (9) from outside the patient's body or drained from within the body.

5 Claims, 4 Drawing Sheets

DEVICE FOR THE EPICARDIAL SUPPORT AND/OR RESUMPTION OF CARDIAC ACTIVITY

BACKGROUND OF THE INVENTION

1. Field of the Invention

The present invention relates to a device for epicardial support and/or the assuming of cardiac activity having a double membrane consisting of an elastic inner membrane and a non-expandable outer membrane as well as a closed cavity formed therebetween which can be inflated and deflated by means of a fluid.

2. Description of Related Art

Such a device—although one which works pericardially—is known for example from the document DE 199 51 220 A1. The device is a minimally-invasive, i.e. percutaneously implantable system for the mechanical support and temporary substitution of the heart's pumping function. After probing the pericardial sac, the device is inserted into the pericardial sac percutaneously in collapsed state or surgically positioned in the pericardial sac at the end of an operation with the double membrane surrounding the right and left ventricles. Thereby the device in its deflated state is so thin that a compression of the adjacent organs will be avoided. Subsequent implantation, the cavity of the double membrane is rhythmically supplied through a connecting tube with a fluid which can either be a gas (helium or $CO_2$) or a suitable liquid. Due to this rhythmic inflation and deflation of the double membrane's cavity and because the outer membrane is not expandable in contrast to the inner membrane, the double membrane surrounding the heart effects pressure transmission and compression of the heart. In so doing, blood is urged from the right ventricle into the pulmonary artery and simultaneously from the left ventricle into the aorta or, with available pumping function of the heart, aids in the systolic ejection of the cardiac muscle.

It is also known that following surgery—even minimally-invasive surgical procedures as in the present case—heart patients need drug therapy to strengthen the heart. The respective medication is thereby normally infused into the pericardial sac through a separately-positioned cardiac catheter. Since this entails additional effort with the associated risks for the patient, the present invention addresses the task of devising this provision of medication to the pericardial sac to be a simpler procedure of substantially lower risk.

SUMMARY OF THE INVENTION

This object is solved by a device for the epicardial support of cardiac activity of the type as indicated at the outset according to the invention in that a second cavity having a fluid-permeable wall limiting the second cavity to the heart is provided at the inward heart-facing side of the inner membrane and that this second cavity can be filled with a fluid through a separate fluid line from outside the patient's body or fluid from within the body can be drained out.

The advantage of the present invention can be seen in particular in that not only drugs can be infused into the pericardial sac without additional effort but also that fluids such as wound secretions, for example, can likewise be drained out. This inventive further development of the device known from the document DE 199 51 220 A1 is of substantial advantage insofar as the device already surrounds the pericardial sac; i.e. was previously implanted. In this regard, the additional disposing of a cardiac catheter as has been necessary to date thus becomes superfluous. Moreover, it is of immense advantage that the device according to the invention allows for a very uniform surface-wide administration of medication, if desired over the entire surface of the heart covered by the double membrane. Finally, it is of great advantage that the administration of medication can be given by means of the separate fluid line independent of location, which is particularly material in the critical post-operative phase.

There are two alternative possibilities provided for configuring the second cavity with its fluid-permeable wall to the heart: firstly, the second cavity can be limited respective the heart by a semi-permeable membrane acting as a fluid-permeable wall. The second cavity would then be formed between the elastic inner membrane of the double membrane and said semi-permeable membrane thereby arranged on the heart side. In so doing, the size of the pores to the semi-permeable membrane then define the molecular size and volume of the medication to be administered.

Alternatively thereto, the second cavity can be constituted by a line arranged on the inward heart-facing side of the inner membrane having defined openings to the heart. A plurality of such lines 10 can of course be arranged on the inward heart-facing side of the inner membrane in order to achieve the most coverage possible in the administration to the cardiac muscle. The lines are thereby comparable to drainage tubes which also exhibit known defined openings.

Since external compression of the epicardial vessels is undesirable after coronary bypass surgery, the double membrane near the large coronary artery preferably comprises variable recesses. This type of double membrane can either be custom-made for a patient or, however, as a further advantageous embodiment provides, customized to the particular requirements of a patient's heart by means of displaceable supports. The variable recesses can thereby be brought into their desired position by the surgeon mechanically manipulating collapsible, flexible bars or half-tubes. These collapsible flexible bars or half-tubes can be held in the desired position during pumping either by their own self-adhering properties, the use of a tissue adhesive, by a support rail or by grooves within the double membrane which force specific positions.

The following will make reference to a figure in describing an embodiment of the invention in greater detail.

DETAILED DESCRIPTION OF THE INVENTION

Figure 1:
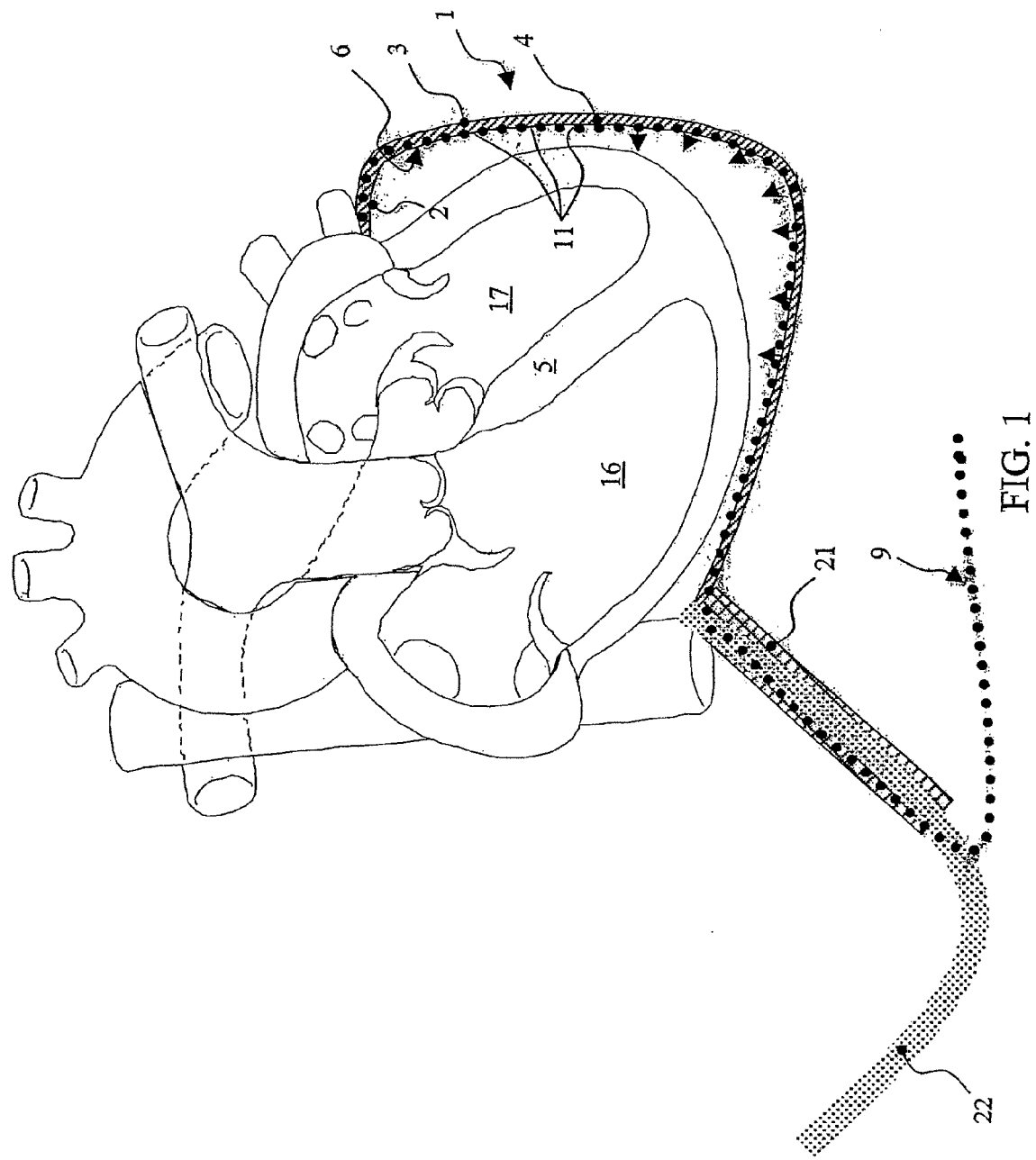
FIG. 1: a schematic representation of the device according to the invention.

FIG. 1 shows a schematic representation of a device for epicardial support and/or the assuming or resuming of cardiac activity having a double membrane 1 consisting of an elastic inner membrane 2 and a non-expandable outer membrane 3 as well as a closed cavity 4 formed therebetween which can be inflated and deflated by means of a fluid. The dotted line at the inward-facing side 6 of the inner membrane 2 to the heart 5 indicates administration of medication, said administration being through openings 11 in a fluid-permeable wall (cf.

Figure 2:
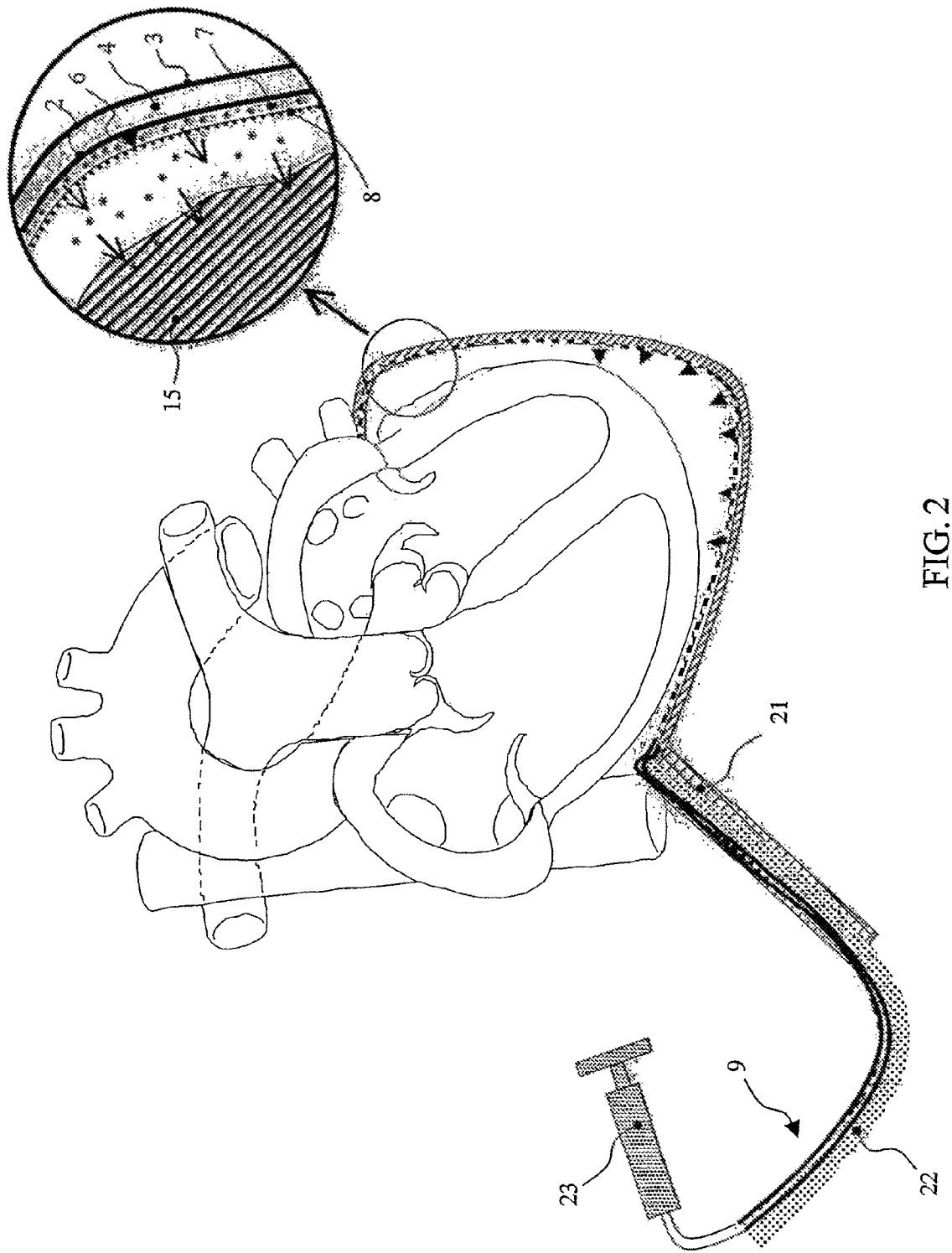
FIG. 2: a schematic representation of the device according to the invention with an enlarged detail depiction of a second cavity comprising a semi-permeable membrane.
Figure 3:
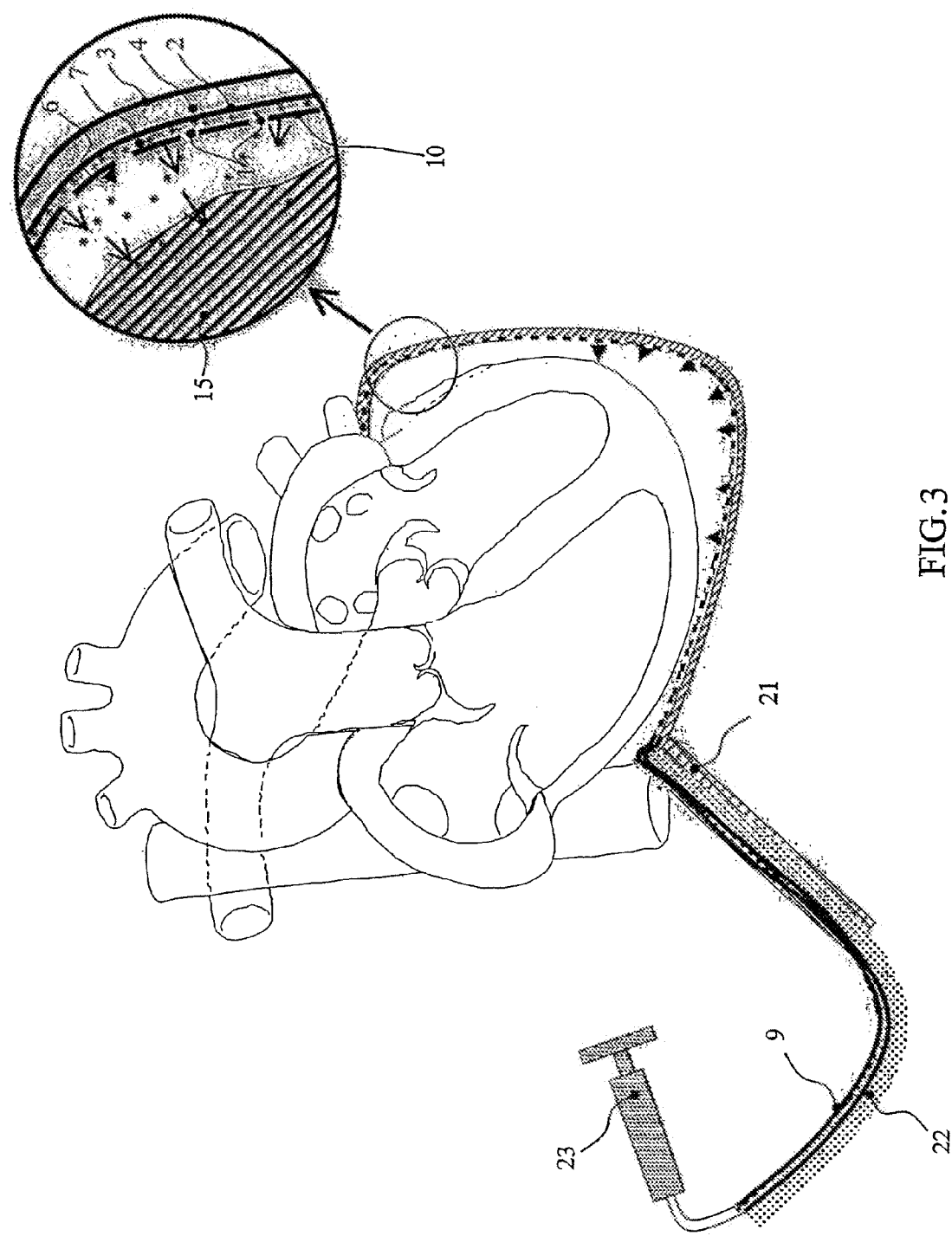
FIG. 3: a representation comparable to that of FIG. 2, wherein this detail enlargement at the upper right now shows a second cavity formed by a line.

FIGS. 2 and 3). The delivery of the medication ensues from outside the body by means of a separate fluid line 9 through an insertion catheter 21 in the skin beside the patient's sternum. Fluid tube 22 likewise runs through this insertion catheter 21 for inflating/deflating the cavity 4 of double membrane 1.

FIG. 2 shows a similar schematic representation of the device according to the invention with a detail enlargement of the double membrane 1 at the upper right corner of FIG. 2. This detail enlargement shows a second cavity 7 joined to the inward-facing side 6 of inner membrane 2 which is limited respective the heart by a fluid-permeable wall in the form of a semi-permeable membrane 8. This second cavity 7 can be used to infuse medication into the pericardial sac from outside the patient by means of an infusion pump 23 and a separate fluid line 9. Here the size of the pores to the semi-permeable membrane 8 define the molecular size and volume of the substance to be administered, this is indicated by the asterisks in cavity 7 and in the vicinity of the cardiac muscle 15.

FIG. 3 shows a representation comparable to that of FIG. 2, whereby the detail enlargement here at the upper right corner of the figure exhibits a cavity 7 formed by one or a plurality of lines 10 with defined openings 11. Here as well, medication—again indicated by asterisks—is supplied to cavity 7, the line(s) respectively, by an infusion pump 23 and a separate fluid line 9. The volume of medication supplied here is dependent on the infusion pressure and the size of the defined openings.

Of course it is also possible with both embodiments of the second cavity 7; i.e., whether formed by a semi-permeable membrane 8 or formed by one or a plurality of lines 10 with defined openings 11 to the heart, to not only administer fluid containing medication but also, for example, drain off wound secretion fluids.

Figure 4:
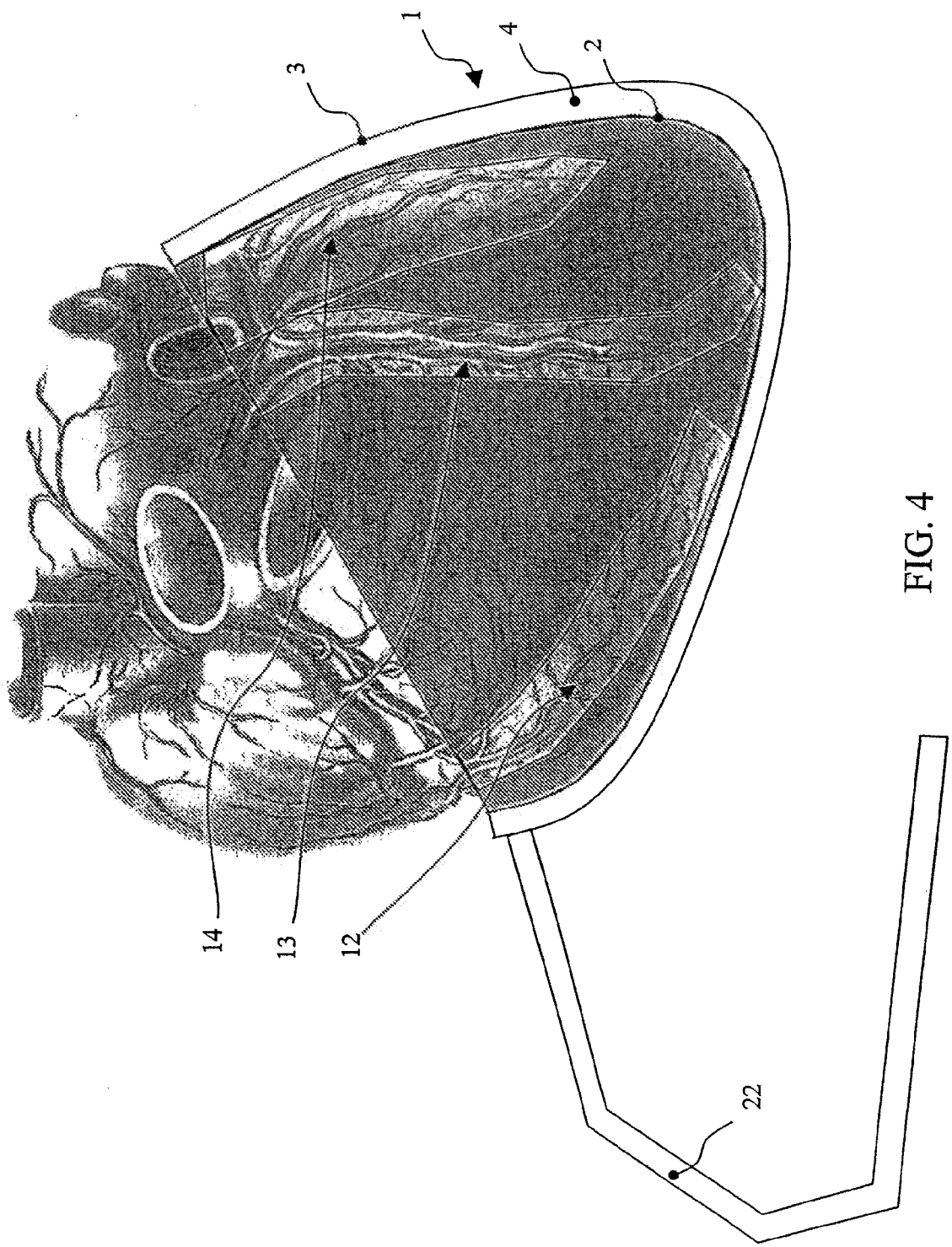
FIG. 4: a representation of the human heart with the inserted device and recesses.

FIG. 4 shows the heart of a patient with a schematically-depicted surrounding double membrane 1, the cavity 4 of which is in turn inflatable and deflatable by means of the fluid tube 22. This embodiment of double membrane 1 exhibits variable recesses 12, 13, 14 in the area of the large coronary artery in order to avoid external compression of the epicardial vessels. These recesses 12, 13, 14 are customizable to the specific requirements of a patient's heart by means of displaceable supports which are not shown here.

What is claimed is:

1. A device for at least one of epicardial support and assuming of cardiac activity, comprising:
    a double membrane formed of an elastic inner membrane and a non-expandable outer membrane, a closed cavity being formed therebetween which can be inflated and deflated by means of a fluid,
    wherein a second cavity delimited by a fluid-permeable wall is provided at an inward facing side of the inner membrane which, in use, faces a patient's heart, and wherein the second cavity is fillable with a fluid supplied through a separate fluid line from one of outside a patient's body and from within the body.

2. The device according to claim 1, wherein the second cavity is limited by a semi-permeable membrane.

3. The device according to claim 1, wherein the second cavity is formed by a line arranged on the inward side of the inner membrane with defined openings.

4. The device according to claim 1, wherein recesses are provided in the double membrane in an area which, in use, is in an area of the large coronary artery.

5. The device according to claim 4, wherein displaceable supports are provided by means of which the recesses are adaptable, in use, to requirements of a particular patient's heart.

* * * * *